United States Patent
Sano et al.

(10) Patent No.: US 7,095,304 B2
(45) Date of Patent: Aug. 22, 2006

(54) SOLENOID AIR VALVE

(75) Inventors: Yoshihiko Sano, Kyoto (JP); Yasutaro Miyatani, Otsu (JP); Hisatomi Matsuda, Mie (JP); Hiroshi Kishimoto, Kyoto (JP); Hiromichi Karo, Kyoto (JP); Ryoichi Fukui, Matsusaka (JP)

(73) Assignee: Omron Healthcare Co., Ltd., Kyoto (JP)

( * ) Notice: Subject to any disclaimer, the term of this patent is extended or adjusted under 35 U.S.C. 154(b) by 0 days.

(21) Appl. No.: 11/176,574

(22) Filed: Jul. 8, 2005

(65) Prior Publication Data

US 2006/0006967 A1    Jan. 12, 2006

(30) Foreign Application Priority Data

Jul. 12, 2004    (JP)    .............................. 2004-204814

(51) Int. Cl.
*H01F 3/00*    (2006.01)

(52) U.S. Cl. ....................... 335/255; 335/261; 335/278; 335/279; 335/281; 335/282; 251/129.15; 251/129.16

(58) Field of Classification Search ....................... 251/129.01–129.22; 335/255, 260, 261, 278, 335/279, 281, 282
See application file for complete search history.

(56) References Cited

U.S. PATENT DOCUMENTS 4,459,991 A    7/1984    Hatschek et al.

5,992,461 A  *  11/1999    Gilmore et al. ........ 137/625.65

FOREIGN PATENT DOCUMENTS

| DE | 29707905 | 8/1998 |
|---|---|---|
| FR | 2470990 | 6/1981 |
| GB | 2064720 A | 6/1981 |
| JP | 09-135817 | 5/1997 |
| JP | 2000-097364 | 4/2000 |
| JP | 2003-225213 | 8/2003 |

OTHER PUBLICATIONS

European Search Report dated Oct. 19, 2005, directed to EP Application No. 05014670.3.

* cited by examiner

*Primary Examiner*—Ramon M. Barrera
(74) *Attorney, Agent, or Firm*—Morrison & Foerster LLP

(57) ABSTRACT

According to a solenoid air valve, a flange portion of a moving core and a flange portion area of a bobbin implement a stop area defining a distance of travel of the moving core in a direction away from a fixed core. An end portion of a shaft portion of the moving core can project outward through an opening of a frame cover, so that a gap between a surface of the frame cover facing the shaft portion and a side surface of the shaft portion (distance: L2) can be minimized. Consequently, a solenoid air valve having a structure allowing improvement in magnetic efficiency by making smaller the gap between the frame and the moving core is provided.

5 Claims, 5 Drawing Sheets

SOLENOID AIR VALVE

BACKGROUND OF THE INVENTION

1. Field of the Invention

The present invention relates to a structure of a solenoid air valve used in a blood pressure monitor or the like.

2. Description of the Background Art

Blood pressure is measured based on information on artery obtained by placing an air bag around human body (brachium, wrist) and inflating the same with air to apply pressure to the human body. When inflated by an air pump, the air bag is closed so as to avoid air leakage. At the time of measurement, deflation control is performed. When the measurement is finished, the inflated air bag needs to be deflated, in order to release the human body from constraint. A solenoid air valve is often used in such a case. A conventional air valve structure is disclosed in Japanese Patent Laying-Open No. 09-135817 (hereinafter, referred to as document 1) and Japanese Patent Laying-Open No. 2000-097364 (hereinafter, referred to as document 2) described below.

According to the air valve structure disclosed in document 1, a nipple is pressed against and brought in contact with a packing portion provided at a tip end of a movable plunger by prescribed elastic force by a spring or the like, thereby controlling air flow rate. In addition, the air valve structure disclosed in document 2 is driven by a moving core or a moving coil, in which a packing is brought in contact with a nipple so as to control a pressure of air that flows, and a viscous member is provided between the moving core or the moving coil and a solenoid fixing member so as to smoothly control air flow rate. In this manner, in the air valve according to the conventional structure, the nipple serving as an air outlet is pressed and closed by sufficient driving force so as to avoid air leakage during inflation. While measurement is being performed and when measurement is finished, the packing is moved in order to control deflation and to release air pressure.

In recent years, in order to improve portability also of a blood pressure monitor, reduction in size of a main unit of the blood pressure monitor is demanded, which means that the air valve contained therein should also be made smaller. The conventional structure, however, suffers from the following problems. The packing for sufficiently covering the nipple portion is necessary for confining air. When the packing is brought in direct contact with the moving core and the moving core is made thinner for size reduction, magnetic reluctance is increased and driving force necessary for pressing the packing is lowered, which results in failure in achieving sufficient sealing and reduction in size.

FIGS. 5 and 6 show a cross-sectional structure of a conventional solenoid air valve 200. A frame 201 has a frame main body 202 and a frame cover 203. Frame main body 202 accommodates a bobbin 241. A coil body 260 is accommodated between an outer circumferential surface of bobbin 241 and an inner circumferential surface of frame main body 202. In addition, in bobbin 241, a fixed core 210 and a moving core 220 serving as a slider are coaxially arranged, and a coil spring 230 applying force in a direction separating fixed core 21 and moving core 220 is accommodated therebetween. In the fixed core, an air passage 211 is provided. A convex nipple (air outlet) 212 is provided at a position of the fixed core opposed to moving core 220, and a rubber packing 250 is embedded in a position of moving core 220 opposed to nipple 212.

In a normal state (a state in which a current is not fed to coil body 260), as shown in FIG. 6, rubber packing 250 of moving core 220 and nipple 212 of fixed core 210 are separated from each other by means of coil spring 230, whereby air can flow out through air passage 211. On the other hand, in a closed state, as shown in FIG. 7, the current is fed to coil body 260, so that magnetic flux is generated by excitation of coil body 260 and moving core 220 is attracted to and brought in contact with fixed core 210. In addition, nipple 212 is pressed by rubber packing 250 to close air passage 211.

Here, reduction in size of air valve 200 structured as above is considered. As shown in FIG. 8, it is possible to make smaller an outer diameter of frame 201, as well as to make smaller an outer diameter $\phi 1$ of fixed core 210 and moving core 220 for ensuring a volume of coil body 260. Taking into account the air flow rate, however, an inner diameter of nipple 212 cannot be made smaller, or a diameter of rubber packing 250 for closing nipple 212 cannot be changed either. Therefore, as shown in FIG. 9, an area of magnetic pole of moving core 220 around rubber packing 250 is made smaller. In such a case, magnetic flux M is concentrated in a narrow area around rubber packing 250, which results in increase in magnetic reluctance, lower efficiency of a magnetic circuit, and lowering in the driving force. Consequently, attractive force of fixed core 210 to be exerted on moving core 220 may extremely be lowered, and leakage of air from nipple 212 is caused. Meanwhile, in order to obtain attractive force equivalent to that in the conventional example in the more compact structure shown in FIG. 8, the current should be increased, which results in increase in a current value.

In addition, as shown in FIG. 10, an end surface portion of moving core 220 opposite to fixed core 210 is covered by bobbin 241 made of resin composed of a non-magnetic material. As a gap L1 comparable to a thickness of the resin is present between frame cover 203 and moving core 220 implementing the magnetic circuit, magnetic reluctance at gap L1 is increased, which may become a factor to lower efficiency of the magnetic circuit.

SUMMARY OF THE INVENTION

The present invention aims to solve the problems of lower driving force and lower efficiency of the magnetic circuit caused when the solenoid air valve is made smaller. From the foregoing, an object of the present invention is to provide a solenoid air valve having a structure allowing improvement in magnetic efficiency by making smaller a gap between a frame and a moving coil.

A solenoid air valve according to the present invention includes: a fixed core fixed and adhered to inside of a frame made of a magnetic material; in the frame, a moving core accommodated in a bobbin made of a non-magnetic material in a manner movable in an axial direction; a gas outlet provided in a surface of the fixed core opposed to the moving core; a packing provided in a surface of the moving core opposed to the gas outlet; force-applying means for applying force to the moving core in a direction away from the fixed core; and a coil body for generating magnetic flux in order to form a magnetic circuit for generating force attracting the moving core toward the fixed core and bringing the same in contact. A stop area defining a distance of travel of the moving core in the direction away from the fixed core is provided between a side surface of the moving core and the bobbin. The frame has a frame main body and a frame cover covering an end surface opposite to a side where the moving core is accommodated. The frame cover has an opening through which the moving core projects outward.

According to the solenoid air valve of the present invention, the stop area defining a distance of travel of the moving core in the direction away from the fixed core is provided between the side surface of the moving core and the bobbin, and the frame cover has the opening through which the moving core projects outward. Therefore, a gap (distance) between a surface of the frame cover facing the shaft portion and the side surface of the moving core should only correspond to a distance of clearance in which the moving core can slide. That is, the gap (distance) can be minimized. Consequently, magnetic reluctance between the frame cover and the moving core due to this gap (distance) can be lowered, whereby efficiency of the magnetic circuit can be improved.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

A structure of a solenoid air valve according to an embodiment of the present invention will be described hereinafter with reference to FIGS. 1 to 3.

Figure 1:
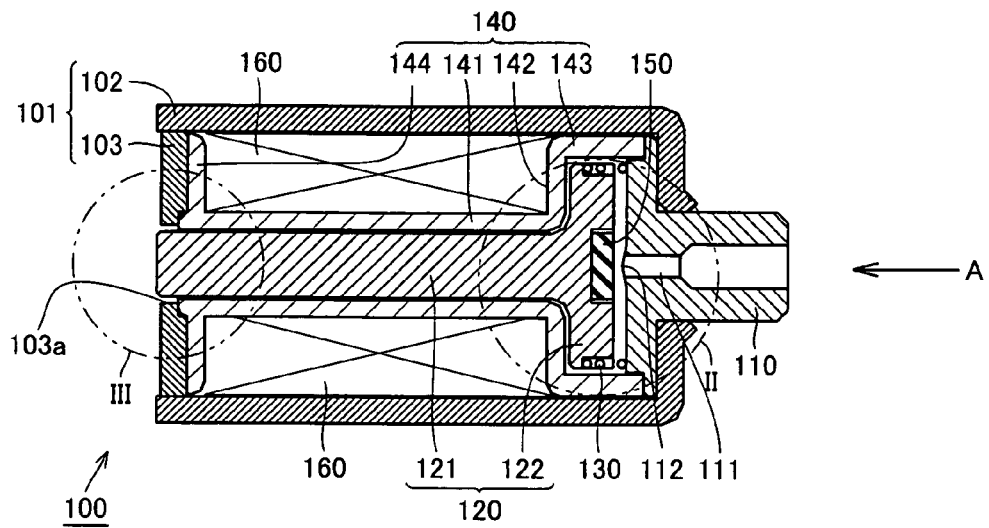
FIG. 1 is a cross-sectional view of a structure of a solenoid air valve according to the present embodiment.
Figure 2:
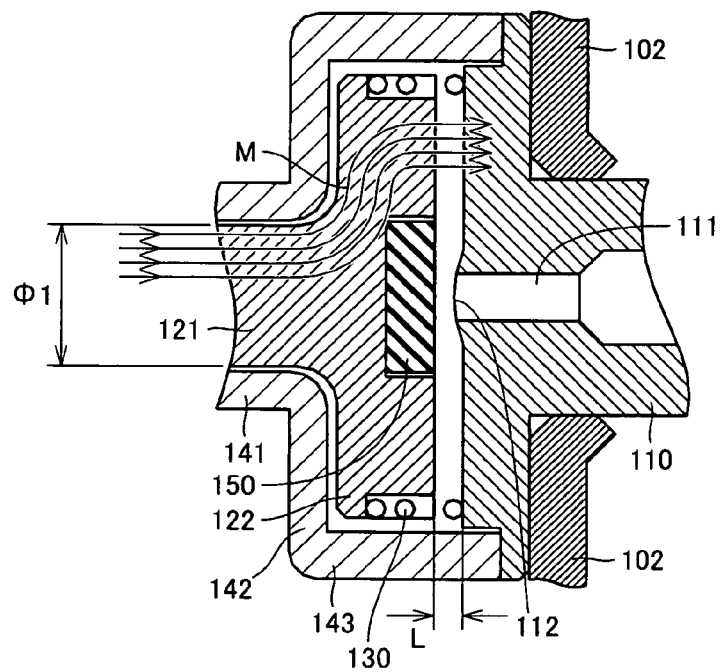
FIG. 2 is a partially-enlarged cross-sectional view of an area encircled by II in FIG. 1.

Referring first to FIG. 1, the structure of a solenoid air valve 100 in the present embodiment will be described. Solenoid air valve 100 includes a frame 101 made of a magnetic material. Frame 101 has a frame main body 102 and a frame cover 103 covering one end portion. For example, SUYB-1 (electromagnetic steel) or the like is used as a magnetic material for frame main body 102 and frame cover 103. A fixed core 110 is fixed and adhered to the inside of frame main body 102 on the other end side, such that a part of the fixed core 110 projects outward. An air passage 111 is provided in fixed core 110, and a convex nipple (air outlet) 112 is provided at a position of fixed core 110 opposed to a moving core 120 which will be described later. In addition, frame main body 102 houses moving core 120 accommodated in a bobbin 140 made of a non-magnetic material in a manner movable in an axial direction.

Movable core 120 includes a flange portion 122 arranged on a side of fixed core 110, provided in a radially projecting manner and having a first diameter, and a shaft portion 121 having a second diameter smaller than the first diameter. A coil spring 130 serving as force-applying means for applying force in a direction separating flange portion 122 and fixed core 110 is accommodated therebetween. A rubber packing 150 is embedded in flange portion 122 of moving core 120 opposed to nipple 112.

Bobbin 140 is provided along an outer circumferential surface of moving core 120, and has a shaft portion area 141 provided along shaft portion 121 of moving core 120, a flange portion area 142 provided along flange portion 122 from shaft portion 121 of flange portion 122, an extension portion area 143 provided along the outer circumferential surface of flange portion 122, and a frame cover area 144 provided along an inner surface of frame cover 103 in an area opposite to flange portion area 142. Therefore, bobbin 140 has a dimension of an outer diameter of flange portion area 142 larger than that of shaft portion area 141.

A coil body 160 for generating magnetic flux is accommodated in a space between the outer circumferential surface of shaft portion area 141 of bobbin 140 and the inner circumferential surface of frame main body 102, in order to form a magnetic circuit for generating force attracting moving core 120 toward fixed core 110 and bringing the same in contact. Coil body 160 has a coil wire diameter of approximately Φ0.1 mm, the number of turns of approximately 1000 and resistance of approximately 30 Ω, and attains a coil current of approximately 80 mA.

Figure 3:
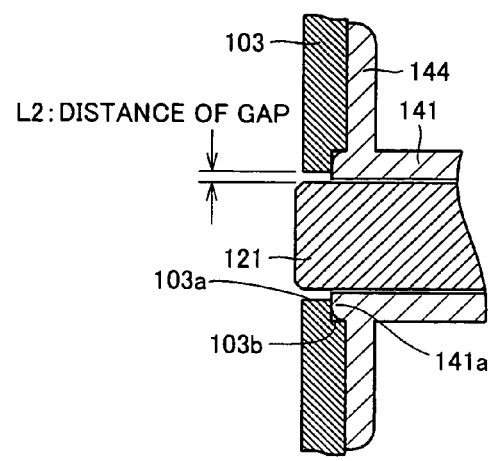
FIG. 3 is a partially-enlarged cross-sectional view of an area encircled by III in FIG. 1.

Referring to FIGS. 1 and 3, frame cover 103 has an opening 103a, through which an end portion of shaft portion 121 of moving core 120 projects outward. In an area where shaft portion area 141 of bobbin 140 intersects with frame cover area 144, a convex portion 141a projecting toward frame cover 103 is provided. In frame cover 103, a concave portion 103b accepting convex portion 141a is provided.

(Function and Effect)

A current is fed to coil body 160 in solenoid air valve 100 structured as above. As shown in FIG. 2, as a sufficient area of magnetic pole is ensured around rubber packing 150 in flange portion 122 of moving core 120, magnetic reluctance is low and flow of magnetic flux M toward fixed core 110 is smooth. In addition, as extension portion area 143 of bobbin 140 made of a non-magnetic material extends along the outer circumferential surface of flange portion 122 of moving core 120, it is ensured that magnetic flux M is guided toward fixed core 110.

Here, it is known that magnetic reluctance of a gap (L) between fixed electrode 110 and flange portion 122 of moving core 120 can be expressed by equation (1) below.

$$R = L/(S\mu_0) \qquad \text{Equation (1)}$$

(magnetic reluctance: R, distance of gap: L, magnetic pole area: S, relative permeability of air: $\mu_0$)

It can be seen from this equation (1) that, for ensuring driving force, an area of magnetic pole (S) should be made larger to lower magnetic reluctance R and enhance efficiency of the magnetic circuit. Paying attention to this equation, the present invention achieves a smaller size of the solenoid air valve in the following manner. Specifically, moving core 120 is shaped like a flange consisting of shaft portion 121 and flange portion 122, in order to ensure sufficient driving force for closing nipple 112 without reducing the area of magnetic pole opposed to a fixed electrode even when the diameter (φ1) of moving core 120 is made smaller for ensuring a volume of the coil.

In addition, coil body 160 is accommodated in the space between shaft portion area 141 of bobbin 140 surrounding shaft portion 121 of moving core 120 and the inner circumferential surface of frame main body 102, so that the dimension of the outer diameter of frame 101 is made smaller while ensuring the volume of a coil portion, and consequently solenoid air valve 100 can be reduced in size.

Moreover, flange portion 122 is provided in moving core 120 and flange portion area 142 along flange portion 122 is provided in bobbin 140, so that a stop area is provided. The stop area defines a distance of travel of moving core 120 in a direction away from fixed core 110 by abutment of a surface of flange portion 122 opposite to fixed core 110 and flange portion area 142 of bobbin 140 when moving core 120 moves along bobbin 140 upon receiving force applied by coil spring 130.

Accordingly, as it is not necessary to define a distance of travel at an end portion of the moving core, the end portion of shaft portion 121 of moving core 120 can project outward through opening 103*a* of frame cover 103. Consequently, as shown in FIG. 3, a gap (distance: L2) between the surface of frame cover 103 facing shaft portion 121 and the side surface of shaft portion 121 of moving core 120 should only correspond to a distance of clearance in which moving core 120 can slide. That is, the gap (distance: L2) can be minimized. As a result, magnetic reluctance between frame cover 103 and moving core 120 due to this gap (distance) can be lowered (see equation 1), whereby efficiency of the magnetic circuit can be improved.

Preferably, convex portion 141*a* and concave portion 103*b* accepting convex portion 141*a* described above are provided between frame cover 103 and bobbin 140, as a positioning area for positioning frame cover 103 and bobbin 140.

Figure 4:
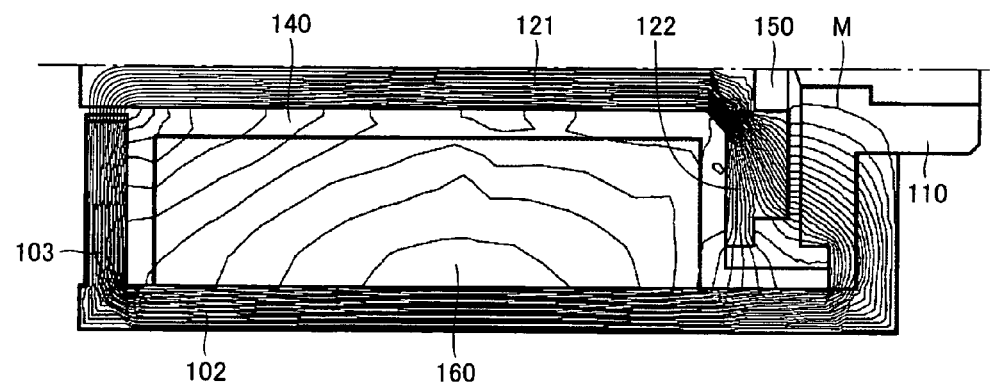
FIG. 4 shows magnetic flux density and a result of analysis of the magnetic flux, using the solenoid air valve according to the present embodiment as a model.
Figure 5:
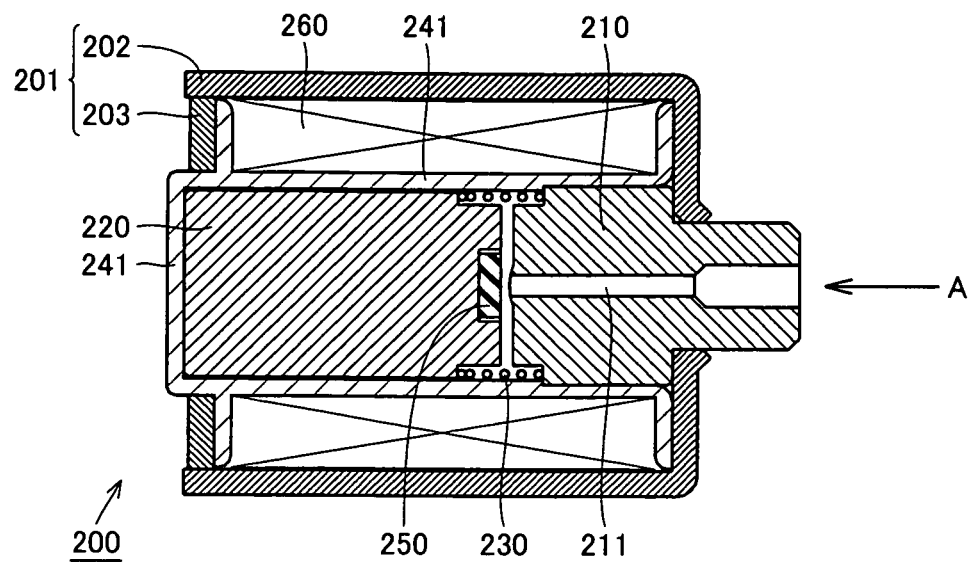
FIG. 5 is a cross-sectional view of a structure of a conventional solenoid air valve.
Figure 6:
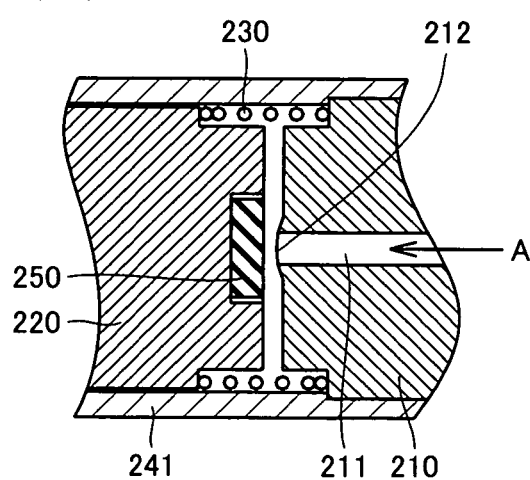
FIG. 6 is a partially-enlarged cross-sectional view of the structure of the conventional solenoid air valve (opened state).
Figure 7:
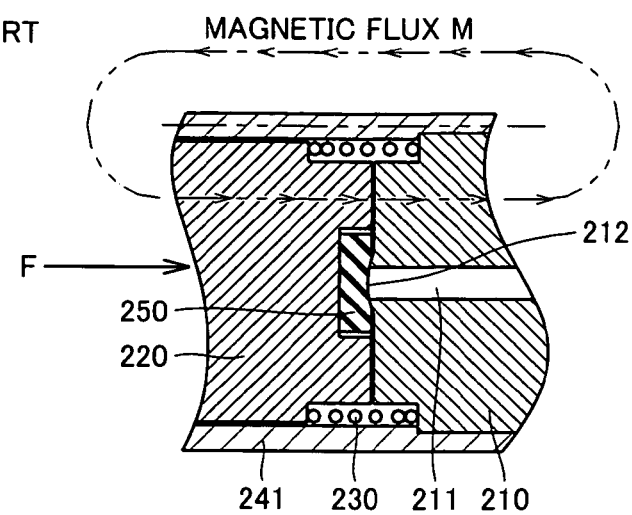
FIG. 7 is a partially-enlarged cross-sectional view of the structure of the conventional solenoid air valve (closed state).
Figure 8:
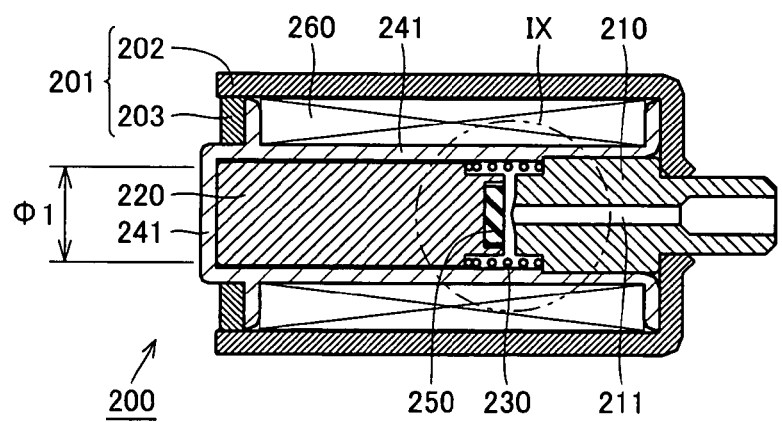
FIG. 8 is a cross-sectional view of a problem showing the conventional solenoid air valve.
Figure 9:
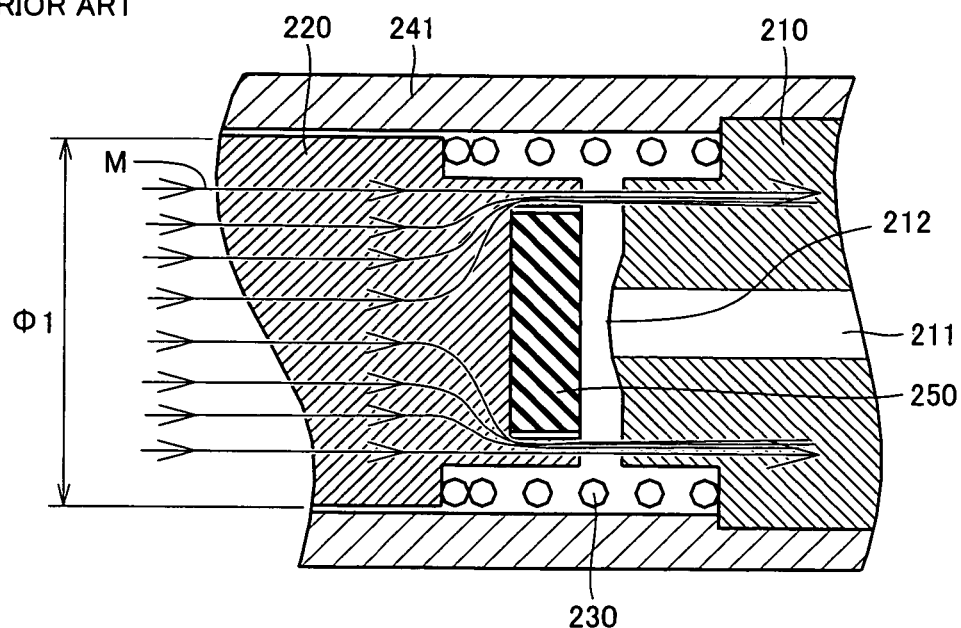
FIG. 9 is a partially-enlarged cross-sectional view showing a first problem of the conventional solenoid air valve.
Figure 10:
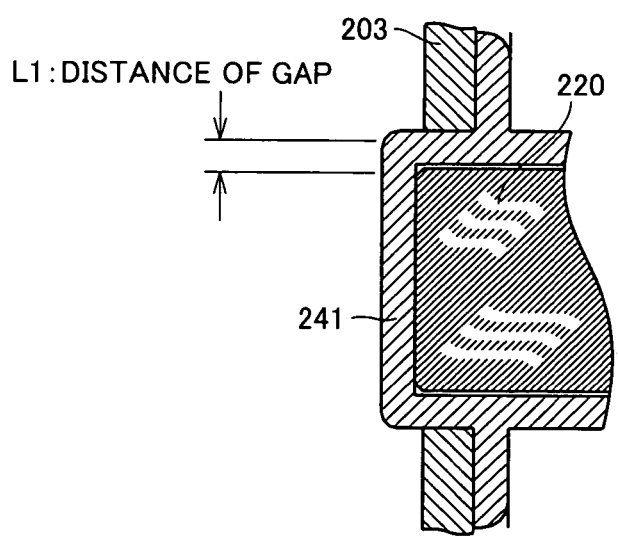
FIG. 10 is a partially-enlarged cross-sectional view showing a second problem of the conventional solenoid air valve.

FIG. 4 shows magnetic flux density and a result of analysis of the magnetic flux, using solenoid air valve 100 according to the present embodiment as a model. The analysis result represents ¼-scale CAE analysis model. The analysis result also shows that magnetic flux M through flange portion 122 of moving core 120 as well as in the gap between the surface of frame cover 103 facing shaft portion 121 and the side surface of shaft portion 121 of moving core 120 smoothly flows, without extremely been concentrated.

In the embodiment described above, the stop area has been formed by flange portion 122 of moving core 120 and flange portion area 142 of bobbin 140. In order to define a distance of travel of moving core 120 in the direction away from fixed core 110, however, a mutual engagement area may separately be provided between the side surface of moving core 120 and bobbin 140, for use as the stop area.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A solenoid air valve comprising:

a fixed core fixed and adhered to inside of a frame made of a magnetic material;

in said frame, a moving core accommodated in a bobbin made of a non-magnetic material in a manner movable in an axial direction;

a gas outlet provided in a surface of said fixed core opposed to said moving core;

a packing provided in a surface of said moving core opposed to said gas outlet;

force-applying means for applying force to said moving core in a direction away from said fixed core; and a coil body for generating magnetic flux in order to form a magnetic circuit for generating force attracting said moving core toward said fixed core and bringing the same in contact; wherein a stop area defining a distance of travel of said moving core in the direction away from said fixed core is provided between a side surface of said moving core and said bobbin, said frame has a frame main body and a frame cover covering an end surface opposite to a side where said moving core is accommodated, and said frame cover has an opening through which said moving core projects outward.

2. The solenoid air valve according to claim 1, wherein said moving core has a flange portion projecting radially outward on a side of said fixed core, said bobbin is provided along an outer circumferential surface of said moving core, and said stop area defines the distance of travel of said moving core in the direction away from said fixed core as a result of abutment of said bobbin and a surface of said flange portion opposite to said fixed core when said moving core moves along said bobbin.

3. The solenoid air valve according to claim 1, wherein a positioning area for positioning said frame cover and said bobbin is provided between said frame cover and said bobbin.

4. The solenoid air valve according to claim 1, wherein said moving core has a flange portion having a first diameter and a shaft portion having a second diameter smaller than said first diameter, and said packing is provided in said flange portion, and said coil body is accommodated in a space between said bobbin surrounding said shaft portion and an inner circumferential surface of said frame.

5. The solenoid air valve according to claim 4, wherein an extension portion area of said bobbin is provided in a manner extending between the outer circumferential surface of said flange portion and the inner circumferential surface of said frame.

\* \* \* \* \*